US008480655B2

(12) United States Patent
Jasperson et al.

(10) Patent No.: US 8,480,655 B2
(45) Date of Patent: *Jul. 9, 2013

(54) DRUG INFUSION SYSTEM PROGRAMMABLE IN FLEX MODE (75) Inventors: Keith E. Jasperson, Andover, MN (US); Thomas J. Valine, Spring Lake Park, MN (US); Frederic J. R. Wahlquist, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 202 days.

This patent is subject to a terminal disclaimer.

(21) Appl. No.: 13/165,329

(22) Filed: Jun. 21, 2011

(65) Prior Publication Data
US 2011/0257625 A1    Oct. 20, 2011

Related U.S. Application Data (63) Continuation of application No. 10/278,769, filed on Oct. 22, 2002, now Pat. No. 7,967,812.

(51) Int. Cl.
*A61M 31/00* (2006.01)
*A61K 9/22* (2006.01)

(52) U.S. Cl.
USPC ..................... 604/890.1; 604/502; 604/65

(58) Field of Classification Search
USPC ............ 604/65, 67, 118, 131, 151, 154–156, 604/890.1, 891.1, 892.1; 128/DIG. 1, 7, 12, 128/13; 316/254, 685, 696; 417/16, 17, 44.2
See application file for complete search history.

(56) References Cited

U.S. PATENT DOCUMENTS

| 3,527,220 | A | | 9/1970 | Summers |
| 3,951,147 | A | | 4/1976 | Tucker et al. |
| 4,146,029 | A | | 3/1979 | Ellinwood, Jr. |
| 4,270,532 | A | | 6/1981 | Franetzki et al. |
| 4,282,872 | A | | 8/1981 | Franetzki et al. |
| 4,308,866 | A | | 1/1982 | Jelliffe et al. |
| 4,373,527 | A | | 2/1983 | Fischell |
| 4,475,901 | A | | 10/1984 | Kraegen et al. |
| 4,525,265 | A | | 6/1985 | Abe et al. |
| 4,559,037 | A | * | 12/1985 | Franetzki et al. ............. 604/151 |
| 4,573,994 | A | | 3/1986 | Fischell et al. |
| 4,619,653 | A | | 10/1986 | Fischell |
| 4,624,661 | A | | 11/1986 | Arimond |
| 4,692,147 | A | | 9/1987 | Duggan |
| 4,731,051 | A | | 3/1988 | Fischell |
| 4,785,799 | A | | 11/1988 | Schoon et al. |

(Continued)

FOREIGN PATENT DOCUMENTS

| DE | 3227518 | 7/1982 |
| EP | 0 649 316 | 10/1993 |

(Continued)

*Primary Examiner* — Kevin Sirmons
*Assistant Examiner* — Andrew Gilbert (57) ABSTRACT A drug infusion system capable of delivering a fluid medication to a patient under direction of a medical professional continually at a basal rate and at an interval rate in each of a plurality of time slots over a specified period of time. The total dose of the fluid medication to be delivered to the patient over the period of time based on the basal rate and the interval rate for each of the plurality of time slots is determined, compared the total dose against a maximum dose. The basal rate is adjusted, if necessary, so that the total dose does not exceed the maximum dose.

20 Claims, 3 Drawing Sheets

U.S. PATENT DOCUMENTS

| | | | |
|---|---|---|---|
| 5,069,668 A | 12/1991 | Boydman | |
| 5,104,374 A | 4/1992 | Bishko et al. | |
| 5,389,078 A * | 2/1995 | Zalesky et al. | 604/151 |
| 5,482,446 A * | 1/1996 | Williamson et al. | 417/474 |
| 5,609,575 A | 3/1997 | Larson et al. | |
| 5,681,285 A | 10/1997 | Ford et al. | |
| 5,685,844 A | 11/1997 | Marttila | |
| 5,713,922 A | 2/1998 | King | |
| 5,772,635 A | 6/1998 | Dastur et al. | |
| 5,782,798 A | 7/1998 | Rise | |
| 5,814,014 A | 9/1998 | Elsberry et al. | |
| 6,010,483 A | 1/2000 | Spencer | |
| 6,070,102 A | 5/2000 | Hartlaub et al. | |
| 6,269,340 B1 | 7/2001 | Ford et al. | |
| 6,551,276 B1 | 4/2003 | Mann et al. | |
| 6,554,798 B1 | 4/2003 | Mann et al. | |
| 6,579,280 B1 * | 6/2003 | Kovach et al. | 604/891.1 |
| 6,585,644 B2 | 7/2003 | Lebel et al. | |
| 6,599,281 B1 | 7/2003 | Struys et al. | |
| 6,669,663 B1 | 12/2003 | Thompson | |
| 6,928,338 B1 * | 8/2005 | Buchser et al. | 700/265 |
| 7,967,812 B2 * | 6/2011 | Jasperson et al. | 604/890.1 |
| 7,968,806 B2 * | 6/2011 | Shelton et al. | 174/520 |
| 2001/0037083 A1 * | 11/2001 | Hartlaub et al. | 604/65 |
| 2002/0019606 A1 | 2/2002 | Lebel et al. | |
| 2002/0077852 A1 | 6/2002 | Ford et al. | |
| 2002/0193679 A1 * | 12/2002 | Malave et al. | 600/407 |
| 2003/0171711 A1 | 9/2003 | Rohr et al. | |
| 2003/0199854 A1 | 10/2003 | Kovach et al. | |
| 2003/0204274 A1 | 10/2003 | Ullestad et al. | |
| 2003/0216682 A1 | 11/2003 | Junker | |
| 2004/0019607 A1 | 1/2004 | Moubayed et al. | |
| 2004/0055649 A1 | 3/2004 | Erickson et al. | |
| 2004/0059315 A1 | 3/2004 | Erickson et al. | |
| 2007/0066956 A1 * | 3/2007 | Finkel | 604/500 |

FOREIGN PATENT DOCUMENTS

| | | |
|---|---|---|
| EP | 0 681 847 A3 | 4/1995 |
| EP | 0 830 170 | 5/1996 |
| EP | 0 681 847 A2 | 4/1997 |
| EP | 1 048 264 | 4/2000 |
| EP | 1 342 482 | 9/2003 |
| FR | 2 792 844 | 4/2000 |
| WO | WO 84/00493 | 2/1984 |
| WO | WO 84/03218 | 8/1984 |
| WO | WO 94/08647 | 4/1994 |
| WO | WO 96/20745 | 7/1996 |
| WO | WO 96/36389 | 11/1996 |
| WO | WO 01/34220 A2 | 5/2001 |
| WO | WO 02/072178 A1 | 9/2002 |
| WO | WO 03/082380 A1 | 10/2003 |
| WO | WO 2004/012043 A2 | 2/2004 |
| WO | WO 2004/026374 A1 | 4/2004 |

* cited by examiner

DRUG INFUSION SYSTEM PROGRAMMABLE IN FLEX MODE

RELATED APPLICATIONS

This application is a continuation of U.S. patent application Ser. No. 10/278,769, filed Oct. 22, 2002, now U.S. Pat. No. 7,967,812, and claims priority therefrom.

FIELD OF THE INVENTION

This invention relates to drug infusion systems and, in particular, drug infusion systems that are programmable by a medical professional.

BACKGROUND OF THE INVENTION

Drug infusion systems can dispense fluid medication, containing a drug, to a patient. Some drug infusion systems are portable, allowing a patient to receive fluid medication while remaining mobile. In addition, some drug infusion systems are implantable to more effectively and less obtrusively dispense such fluid medication to a patient.

Devices and techniques for treating a patient by drug infusion, and/or by electrical stimulation of a person's central nervous system, are well known in the prior art. For instance, U.S. Pat. No. 5,782,798, Rise, entitled Techniques For Treating Eating Disorders By Brain Stimulation and Drug Infusion; U.S. Pat. No. 5,814,014, Elsberry et al, Techniques of Treating Neurodegenerative Disorders by Brain Infusion, each assigned to Medtronic, Inc., Minneapolis, Minn., disclose such devices and techniques are hereby incorporated by reference.

Another example of a drug infusion device is shown in U.S. Pat. No. 3,527,220, Summers, entitled Implantable Drug Administrator, an implantable drug administrator having a refillable bladder which can be filled with a drug and a pump for selectively pumping the drug from the bladder into any desired area of the body. The administrator includes an indicator for indicating when the desired amount of the drug has been injected.

In U.S. Pat. No. 3,951,147, Tucker et al, entitled Implantable Infusate Pump, a rechargeable infusate pump for implantation in the human body can be refilled periodically by injection through an inlet septum under the skin. A conduit conducts fluid to an infusion site in the body. The pump outlet includes a special controller flow controller which is able to very accurately meter the infusate to the selected body site.

A problem with these implantable drug infusion devices is that there is no way to provide a simple external means to select the dosage amounts and intervals from a wide range of possible doses and intervals, and verify that a desired change had been made.

U.S. Pat. No. 4,146,029, Ellinwood, Self-Powered Implanted Programmable Medication System and Method, discloses a device and method for dispensing medication internally of the body utilizing an implanted system which includes medication storage and dispensing control circuitry having control components which may be modified by means external of the body being treated to control the manner of dispensing the medication within such body. In particular, extracorporeal control means may provide some measure to achieve selected medication programs corresponding to particular codes.

U.S. Pat. No. 4,692,147, Duggan, Drug Administration Device, assigned to Medtronic, Inc., Minneapolis, Minn., discloses an implantable drug administration device which can be non-invasively programmed to change both the dosage amount and the dosage interval. Verification of the received dosage and interval commands is achieved by means of an audio transducer which is attached to the device case.

The implantable drug administration device described in Duggan allows a medical professional to program to the delivery rate of a drug contained in the reservoir of the device over a specified interval. The process, however, to achieve an even reasonably complex dosing regimen is laborious and time consuming. Each interval must be specified and the particular delivery rate must be individually programmed. For all but the simplest of dosing regimens, this system is not only laborious and takes too long to program but also prone to error due to the painstaking programming steps which must be accomplished.

BRIEF SUMMARY OF THE INVENTION

In a first embodiment, the present invention provides a drug infusion system capable of delivering a fluid medication to a patient under direction of a medical professional. A drug delivery module is capable of delivering the fluid medication to the patient continually at a basal rate and is capable of delivering the fluid medication at an interval rate in each of a plurality of time slots over a specified period of time. A controller, programmable by the medical professional, is operatively coupled to the drug delivery module to control the basal rate and the interval rate at which the fluid medication is delivered to the patient. The controller, upon being programmed by the medical professional to deliver an interval rate for at least one of the plurality of time slots, determines a total dose of the fluid medication to be delivered to the patient over the period of time based on the basal rate and the interval rate for each of the plurality of time slots, compares the total dose against a maximum dose and adjusts the basal rate, if necessary, so that the total dose does not exceed the maximum dose.

In another embodiment, the present invention provides a drug infusion system capable of delivering a fluid medication to a patient under direction of a medical professional. A drug delivery module is capable of delivering the fluid medication to the patient continually at a basal rate and is capable of delivering the fluid medication at an interval rate in each of a plurality of time slots over a specified period of time, the interval rate being different from the basal rate. A controller, programmable by the medical professional, is operatively coupled to the drug delivery module to control the basal rate and the interval rate at which the fluid medication is delivered to the patient. The controller, upon being programmed by the medical professional to deliver an interval rate for at least one of the plurality of time slots, determines a total dose of the fluid medication to be delivered to the patient over the period of time based on the basal rate and the interval rate for each of the plurality of time slots and adjusts the basal rate to maintain the total dose.

In a preferred embodiment, the controller may be programmed separately for each day of a week.

In another embodiment, the present invention provides a method of delivering a fluid medication to a patient under direction of a medical professional. Fluid medication is delivered to the patient through an implanted device continually at a basal rate and capable of delivering the fluid medication at an interval rate in each of a plurality of time slots over a specified period of time, the interval rate being different from the basal rate. The basal rate and the interval rate at which the fluid medication is delivered to the patient are controlled. A total dose of the fluid medication to be delivered to the patient over the period of time based on the basal rate and the interval rate for each of the plurality of time slots is determined. The basal rate is then adjusted to maintain the total dose.

In a preferred embodiment, the total dose equals the maximum dose.

In a preferred embodiment, the interval rate may be programmed individually for each of the plurality of time slots.

In a preferred embodiment, the period of time is a day, the total dose is a daily dose and the maximum dose is a desired daily dose.

In a preferred embodiment, days of each of the week may be grouped together and programmed together.

In a preferred embodiment, a graphical display of the interval rate in each of the plurality of time slots is provided.

In a preferred embodiment, the graphical display is provided to the medical professional.

In a preferred embodiment, the graphical display comprises a bar graph having a bar for each of the plurality of time slots and wherein in the bar has a length proportional to the basal rate and the interval rate.

In a preferred embodiment, the patient can switch between the basal rate and the interval rate in at least one of the plurality of time slots.

DETAILED DESCRIPTION OF THE INVENTION

The entire content of U.S. patent application Ser. No. 10/278,769, filed Oct. 22, 2002 is hereby incorporated by reference.

Figure 1:
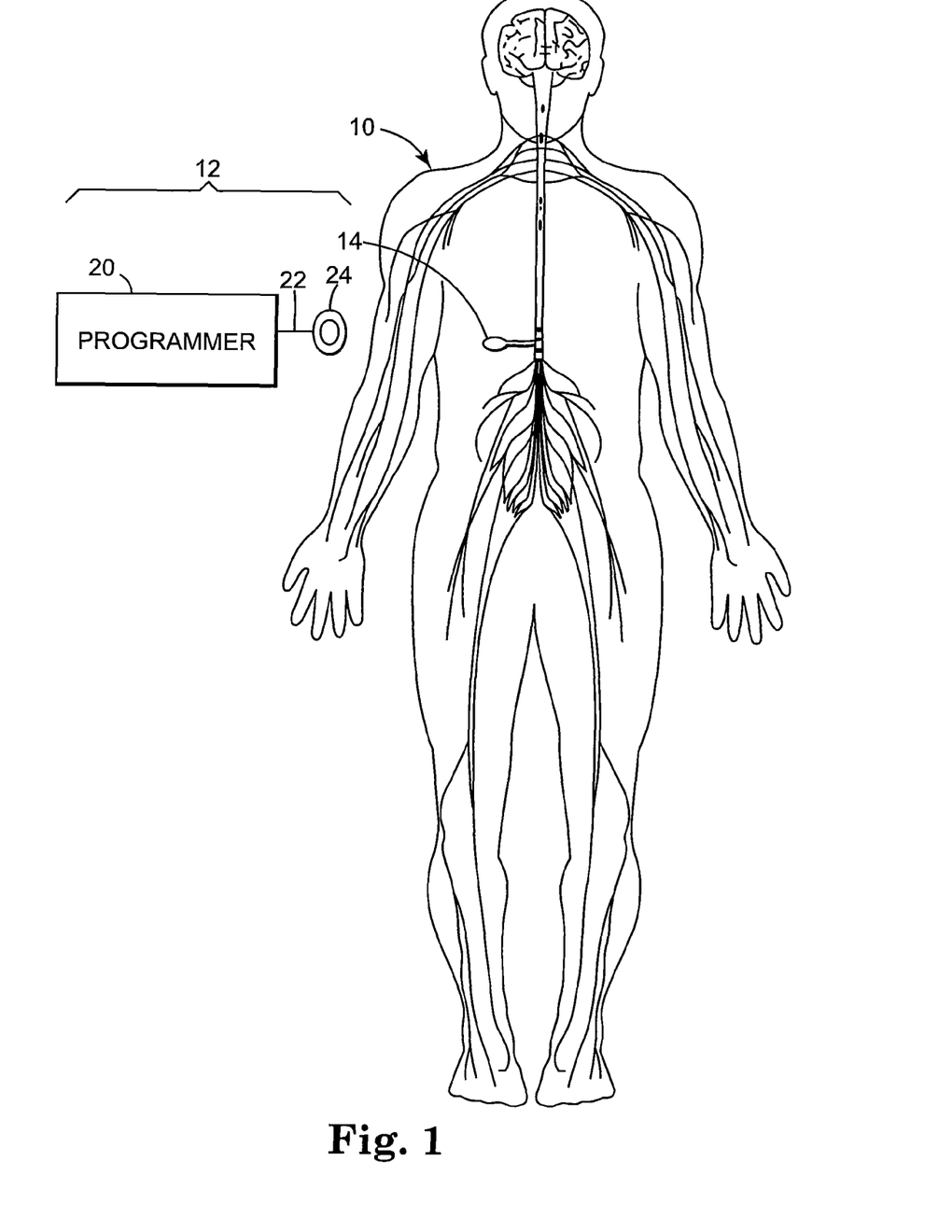
FIG. 1 is a schematic view of a drug infusion system of the present invention having a drug infusion device implanted within the patient's body.

FIG. 1 is a schematic view of drug infusion system 12 of the present invention. Implantable drug infusion device 14 is shown implanted within the body of patient 10. Drug infusion device 14 is programmable through a telemetry link from programmer 20, which is coupled via a conductor 22 to a radio frequency antenna 24. Drug infusion device 14 could be, but is not limited to being, a pump for infusing fluid medication into a patient's body. Methods of communicating, using radio frequency telemetry, with implanted treatment devices in order to program such implanted drug infusion devices, are well known in the art.

Figure 2:
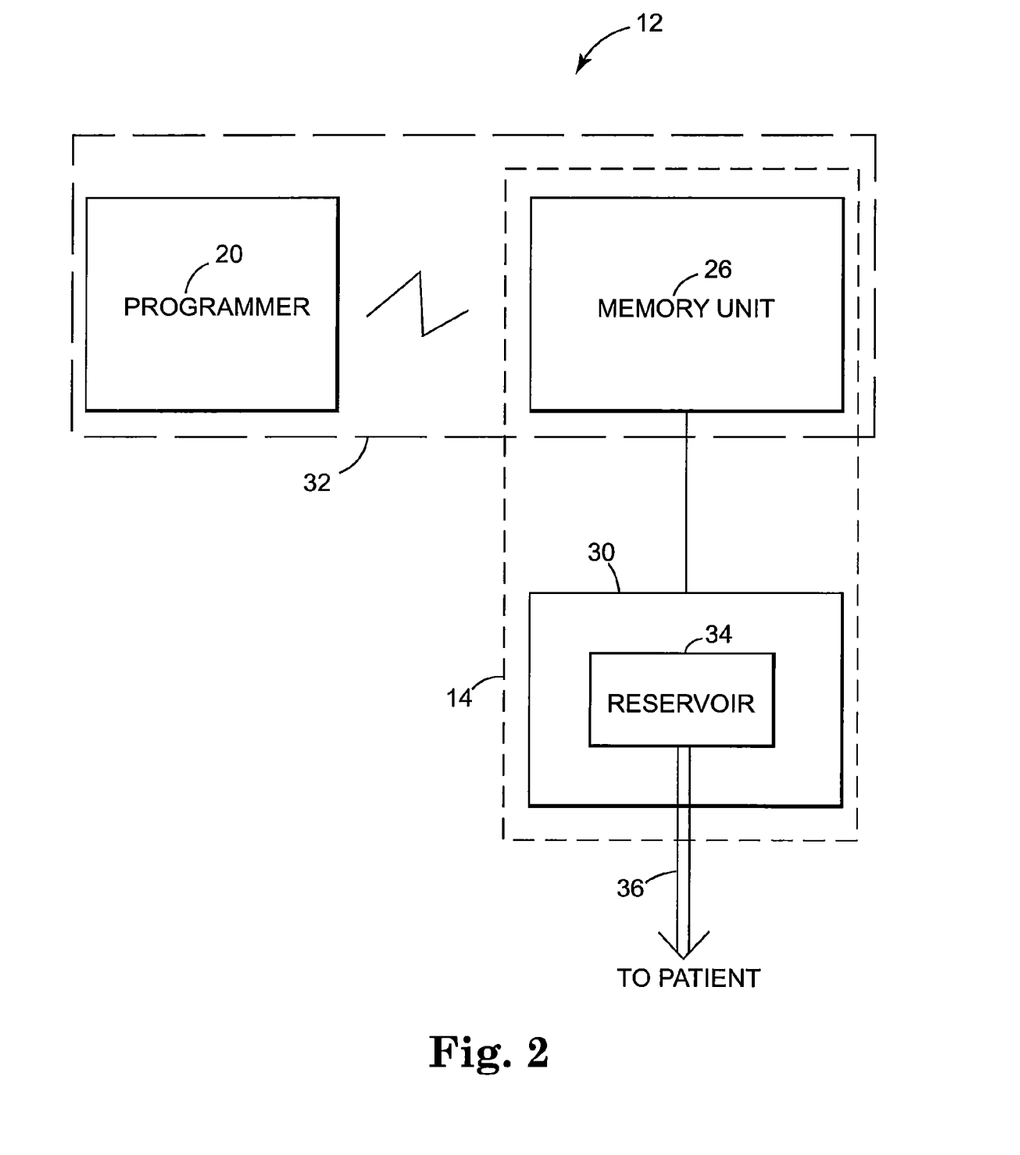
FIG. 2 is a block diagram of a drug infusion system of the present invention having an implantable drug infusion device and an external programmer.

FIG. 2 is a block diagram of drug infusion system 12 having an implantable drug infusion device 14. Drug infusion device 14 consists of an internal memory unit 26 containing memory and registers which provide internal drug delivery instructions to drug delivery module 30. External programmer 20 acts as an input-output device for drug infusion system 12 and also provides computational support for memory unit 26. Memory unit 26 and programmer 20, operating together, function as a controller 32 controlling drug delivery module 30 in the delivery of fluid medication to patient 10. In general, drug delivery module 30 is a pump for infusing a fluid medication, including a drug or a combination of drugs, to patient 10. Drug delivery module 30 has a reservoir 34 for holding the fluid medication to be infused and is coupled to patient 10 through catheter tubing 36. Such drug delivery modules 30 are well known in the art.

Memory 26 receives programming information, via telemetry, from programmer 20 through conventional means. Programming information, once stored in memory unit 26, provides the dosing regimen to be performed by drug delivery module 30.

Drugs may be provided to a patient 10 by drug delivery module 30 at a predetermined dosage, generally calculated as an amount of drug provided to patient 10 in a predetermined period of time. It is typical to specify such dosage as an amount of drug, e.g., measured in milligrams, per day, or per twenty-four hour period. This dosage amount provides the medical professional with information about the probable efficacy of the drug and potential harmful side effects of the drug on patient 10. Typically, enough drug must be administered in order to have a therapeutic effect. At the other end of the scale, the amount of the drug typically must be limited to a maximum amount, typically referred to as the maximum daily dose, in order not to avoid potentially damaging side effects.

It is typically relatively easy for a medical professional to determine the proper maximum daily dose for patient 10 that, hopefully, will provide a therapeutic benefit while not producing significant harmful side effects.

However, patient 10 may have a need for differing amounts of a given drug during different time intervals. For example, a patient may have a greater need for a drug which provides therapeutic pain relief during the nighttime hours in order to allow the patient to sleep. Likewise, this same patient may have less of a need for the drug during active daytime hours when the patient is concentrating on other activities. In order to provide the maximum therapeutic effect of the drug during the high-need nighttime hours and to minimize potentially harmful side effects, the drug infusion device may be programmed to deliver a greater amount of the drug during certain time intervals, in this case during the nighttime hours and a lesser amount of the drug during the normally active daytime hours. By cutting down of drug delivery during the active daytime hours, a greater amount of the drug may be delivered by the drug infusion device during the nighttime hours and still keep the maximum daily dose within acceptable limits.

An example of a drug infusion regimen which may be programmed into an implanted drug infusion device is shown in Table I.

TABLE I

| Time Slot | Time of Day | Delivery Rate | Drug Delivered |
|---|---|---|---|
| 1 | 00:00 hours-03:00 hours | 35 mg/hr | 105 mg |
| 2 | 03:00 hours-05:00 hours | 25 mg/hr | 50 mg |
| 3 | 05:00 hours-20:00 hours | 20 mg/hr | 300 mg |
| 4 | 20:00 hours-22:00 hours | 25 mg/hr | 50 mg |
| 5 | 22:00 hours-24:00 hours | 35 mg/hr | 105 mg |

In the drug infusion regimen illustrated in Table I, patient 10 receives a higher drug delivery rate during the nighttime hours between 20:00 hours in the evening (8:00 p.m.) and 05:00 hours in the morning (5:00 a.m.). During the normally active daytime hours between 05:00 hours (5:00 a.m.) and 20:00 hours (8:00 p.m.), patient 10 receives a lower drug delivery rate of 20 milligrams per hour, receiving a total of 300 milligrams of drug during this period.

During this time period patient 10 receives a total dose of 610 milligrams over the twenty-four hour period, representing the daily dose for patient 10. However, this daily dose is not provided evenly over the twenty-four hour period.

In order to program the drug infusion device to delivery the varying doses in different time intervals, as, for example, throughout the day, it may be necessary to enter a large number of programming steps into the drug infusion device. In the rather simple example provided above, in which patient 10 is simply provided with an increased dosage during the nighttime hours, stepped up in two increments, a total of five different programming steps must be accomplished. Even if the highest dosage rate from 8:00 p.m. to 5:00 a.m. did not occur in different day periods (and, hence, steps 1 and 5 could be combined), a total of four programming steps would still be required.

U.S. patent application Ser. No. 09/302,613, filed Apr. 30, 1999, entitled Generic Multi-Step Therapeutic Treatment Protocol, the contents of which is hereby incorporated by reference, describes one method of programming a complex continuous dosing regimen. Although the programming protocol described in this patent application may have groups and may have repeated segments, and although it is possible to make the timing of such programming steps relative to other events or to a particular time of day, it is still necessary to program each program step individually.

The complexity of such programming has two effects on the efficacy of the drug infusion device. First, with an increase in the number of data entry steps to be completed, the potential for errors increases. Second, the tedious nature of the data entry tends to discourage medical professionals from prescribing complex dosing regimens. Without the prescription by the medical professional of such complex dosing algorithms, patient 10 will not obtain the benefits that such a complex dosing regimen would provide.

The drug infusion system 12 and method of the present invention provides a simpler technique for programming memory unit 26 of drug infusion device 14 allowing drug delivery module 30 to provide a complex dosing regimen to patient 10. Table II below illustrates a complex dosing regimen with same drug delivery result as the complex dosing regimen described in Table I, but in a way that is much easier to program.

TABLE II

| Time Slot | Time of Day | Basal Rate | Interval Rate | Total Rate | Drug Delivered |
|---|---|---|---|---|---|
| 1 | 00:00 hours-03:00 hours | 20 mg/hr | +15 mg/hr | 35 mg/hr | 105 mg |
| 2 | 03:00 hours-05:00 hours | 20 mg/hr | +5 mg/hr | 25 mg/hr | 50 mg |
| 3 | 05:00 hours-20:00 hours | 20 mg/hr | 0 mg/hr | 20 mg/hr | 300 mg |
| 4 | 20:00 hours-22:00 hours | 20 mg/hr | +5 mg/hr | 25 mg/hr | 50 mg |
| 5 | 22:00 hours-24:00 hours | 20 mg/hr | +15 mg/hr | 35 mg/hr | 105 mg |

Memory 26 may be programmed according to the complex dosing regimen described in Table II so that drug delivery module 30 will deliver whatever drug or drugs are contained in reservoir 34 to patient 10 at a basal delivery rate, or basal rate, of 20 milligrams per hour. In addition to fixed, memory unit 26 may be programmed at an interval rate which can vary for each separate interval period. In the complex dosing algorithm described in Table II, an interval rate of +15 milligrams per hour should be programmed for time slot number 1, namely the time slot from midnight to 3:00 a.m. The interval rate of +15 milligrams per hour is added to the basal rate of 20 milligrams per hour to achieve a total delivery rate for this time period of 35 milligrams per hour. Note that 35 milligrams per hour is the same total delivery rate of medication as specified for the same time slot in the complex dosing regimen described in Table I. This represents the higher dosing rate for patient 10 during the inactive nighttime hours. During time slot 2, from 3:00 a.m. to 5:00 a.m., the interval rate is decreased to +5 milligrams per hour. Again, this interval rate is added to the basal of 20 milligrams per hour resulting in a total delivery rate during time slot 2 of 25 milligrams per hour. During the normally active daytime of time slot 3, from 5:00 a.m. to 8:00 p.m., when a lesser amount of drug is desired to be delivered to patient 10, the interval rate is cut to zero. With the interval rate of zero being added to the basal rate, the total delivery rate results in 35 milligrams per hour. As nighttime approaches, time slot 4, from 8:00 p.m. to 10:00 p.m., the interval rate is again increased to +5 milligrams per hour. Added to the basal rate, time slot 4 results in a total delivery rate of 25 milligrams per hour. Time slot 5, from 10:00 p.m. to midnight, is programmed similarly to time slot 1, having an interval rate of +15 milligrams per hour. Added to the basal rate, the total delivery rate for time slot 5 is 35 milligrams per hour.

While the complex dosing regimen described in Table II has interval rates which are equal or greater than zero, resulting in a total delivery rate for each time slot that is equal to or greater than the basal rate, it is to be recognized and understood that interval rates which are negative are also possible. For example, if the interval rate programmed for time slot 3 was −5 milligrams per hour, then this interval rate would still be added to the basal rate (minus 5 milligrams per hour plus 20 milligrams per hour) resulting in a total delivery rate for that slot of 15 milligrams per hour, which is less than that of the basal rate of 20 milligrams per hour.

It is also possible that instead of programming the interval rate as a positive or negative number, the interval rate could be a magnitude and the programming step could also, optionally, include whether to add or subtract the magnitude of the interval rate to or from the basal rate.

The complex dosing regimen described in Table II in terms of milligrams of drug which is then delivered over a period of time, resulting is a delivery rate of an amount of drug per unit time. Since drug delivery module 30 is pumping a volume of liquid, and not an amount of drug, controller 32 may convert a programmed amount of drug, e.g., 20 milligrams, by knowing the concentration of the drug contained in the reservoir 34 of drug delivery module 30, into a volume of drug to be delivered per unit time.

Conversely, it is also possible that memory unit 26 may be programmed by programmer 20 using a volume of drug to be administered per unit time. If this is the case, controller 32 may, or may not, use the concentration of the drug to determine the amount of drug to be delivered per unit time to patient 10.

It will be recognized and understood that the complex dosing regimen described in Table II is exemplary only and many other dosing regimens, both complex and simple, are possible.

An advantage of programming drug infusion system 12 with both a basal rate and an interval rate is that it may be easier for a medical professional think in terms of increasing or decreasing a dose in a particular time interval, rather than in fixed dosage amounts. In addition, it is much easier to implement a patient bolus or a physician bolus, in which the patient or physician, respectively, may temporarily increase the amount of drug (delivery rate) to be given to the patient. An example of such a patient bolus is with pain medication. The drug infusion system 12 is programmed to deliver a constant of pain medication, a basal rate, or perhaps a basal along with additional programmed interval rates for specific time periods or as a result of specific events. In addition, patient 10 may be provided with means to enable an extra amount of drug (an increased delivery rate) for an interval in time when the patient needs an additional amount of pain relieving medication. Programmed as described in this invention, the basal rate may remain the same and an interval rate based upon the patient bolus may be added to the basal rate. It is also possible, if desired, to allow a patient bolus on top of not only the basal rate but also on top of any additional interval rate already programmed into drug infusion system 12.

As can be seen in Table II, while it is easy for the medical professional programming drug infusion system 12 to determine the individual dosing rate and amount for a given interval, it is more difficult to determine the total dose provided to patient 10 over the entire programmed event schedule, such as a day or a twenty-four hour period. It is important for most drug delivery protocols to know the total daily dosage for a drug so that it can be compared with the maximum daily dose for each patient 10. Or alternatively, the medical professional may have in mind an intended daily dose for patient 10 and may program that dose as the maximum daily dose into drug infusion device 10. The total amount of drug actually delivered to patient 10 in one twenty-four hour period (midnight to midnight) is 610 milligrams. However, this is not easily recognizable from the programmed steps illustrated.

When the medical professional programs a basal rate and specific interval rates into memory unit 26 using programmer 20, controller 34 calculates the total daily dose provided by the programmed steps, including the amount to be delivered by the basal rate and by the all of the intervals rates (whether additive or subtractive) and compares that total dose against a maximum dose, such as the maximum daily dose for patient 10 or a preferred total daily dose for patient 10 specified by the medical professional. If the total amount of drug to be delivered exceeds the maximum dose, controller 32 adjusts the basal rate so that the total dose to be delivered to patient 10 does not exceed that maximum dose.

For example, with the complex dosing regimen specified in Table II, a total daily dose of 610 milligrams of drug would be provided to patient 10. If the maximum daily dose for patient 10, as determined by the medical professional and programmed into controller 32 using programmer 20, is 500 milligrams, then 110 milligrams of drug must be trimmed from the basal rate. In this case, the interval steps would provide a total of 310 milligrams of drug during the twenty-four hour period. Subtracting the 310 milligrams of drug to be provide by the interval steps from the maximum daily dose of 500 milligrams, leaves a total of 190 milligrams of drug to be delivered by the basal rate. Since there is a total of twenty-four hours in a day, the basal rate is then adjusted 12.66 milligrams (190 divided by 15) per hour.

The resulting calculated basal rate could be implemented or, alternatively, could be communicated, e.g., displayed, to the medical professional via programmer 20 for confirmation or adjustment by the medical professional. Upon seeing that the programmed intervals steps has resulted in basal rate being cut from 20 milligrams per hour to 12.66 milligrams per hour, the medical professional may decide whether this result is acceptable or whether other adjustments are preferred. For example, the medical professional may decide to adjust one or more of the interval rates in order to maintain the basal rate at a previous higher rate. Alternatively, the medical professional could choose to increase the maximum dose to allow continuance of the 20 milligrams per hour basal rate.

This calculation and adjustment works equally well with specified preferred daily doses as it does with maximum daily doses. The methodology works exactly the same.

While it is contemplated that any or all of the calculations performed by controller 32 could be performed in either programmer 20 or memory unit 26, it is recognized that drug delivery device 14, being an implantable device, will probably have a limited amount of processing power and energy source. Therefore, it is preferred that the calculations referred to as being performed by controller 32 (encompassing both programmer 20 and memory unit 26) actually be performed by programmer 20, in order to control the precious resources of implantable drug infusion device 14.

In addition, it may be desirable to specify a preferred daily dose which the drug infusion system 12 will maintain. In this case, if the specified basal rate, if any, and the specified interval rates, if any, either exceed or fall under the preferred daily dose, drug infusion system 12 may calculate a new basal rate which will ensure that the preferred daily dose will be achieved. If the preferred daily dose is exceeded, drug infusion system 12 may decrease the basal rate until the preferred daily dose is obtained. Conversely, if the preferred daily dose is not reached, drug infusion device may increase the basal rate until the preferred daily dose is obtained. Again, any such decreases or increases may be performed after consultation with the medical professional.

While the discussion above has involved a daily dose, either maximum or preferred, it is to be recognized and understood that other time periods are also contemplated. Instead of a daily dose, calculations could be based upon a hourly dose, a weekly dose or any other desired period of time.

Figure 3:
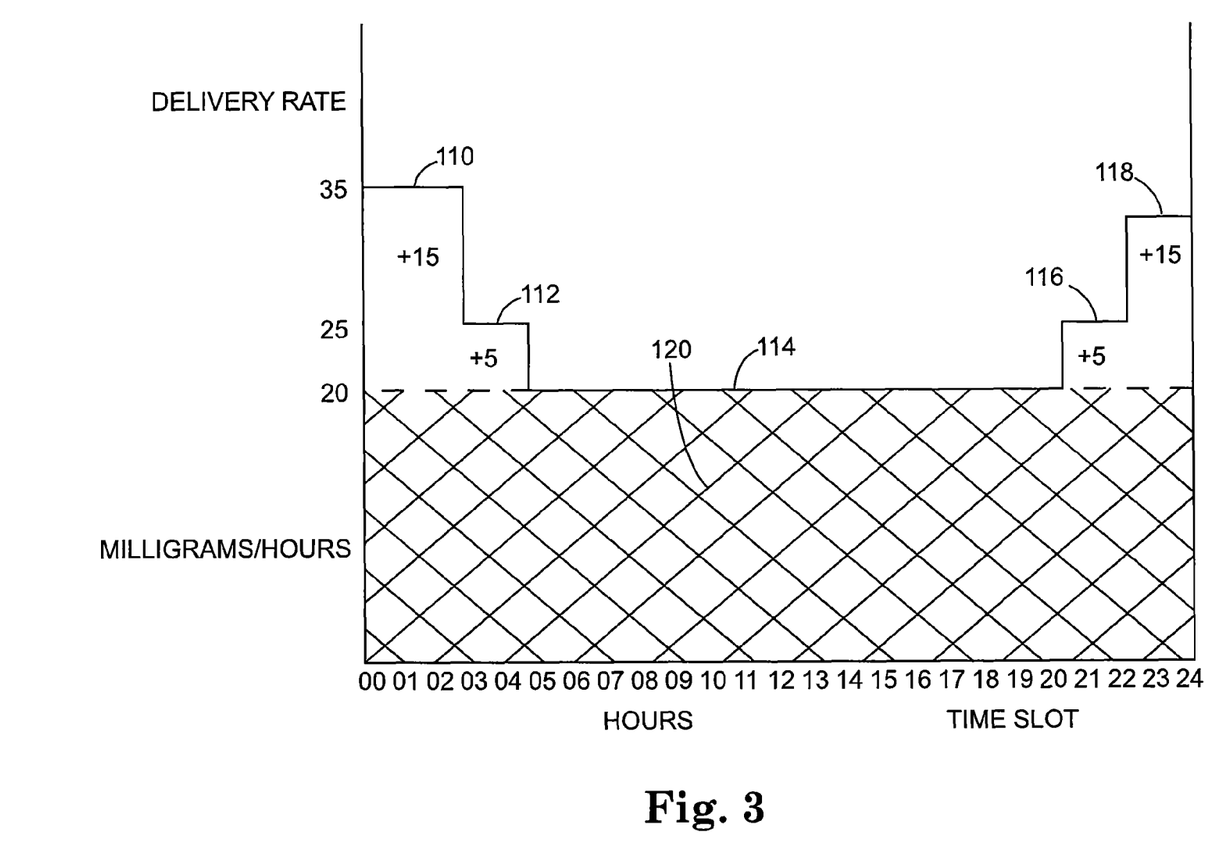
FIG. 3 is a graphical representation of a preferred interface with the drug infusion system of the present invention.

FIG. 3 illustrates a graphical representation of the complex dosing regimen specified in Table I. The horizontal axis (abscissa) in FIG. 3 represents a plurality of time slots, in this case each of the twenty-four hours of day. The vertical axis (ordinate) in FIG. 3 represents a fluid medication delivery rate. The graphical representation could represent a single day's dosing regimen which is then repeated day after day until modified, or until another specified program takes over. Alternatively, the graph may represent a dosing regimen for a particular day of the week or a group of particular days of the week, e.g., Monday through Friday. Other dosing regimens, and other graphical representations, could represent different time periods or different days of the week, e.g., the weekend or Saturday or Sunday.

Bar 110 is a graphical representation of the drug delivery specified in time slot 1 of Table II, namely a total delivery rate of 35 milligrams per hour for a three hour time period, in this case from midnight to 3:00 a.m. Shorter bar 112 is a graphical representation of the total drug delivery rate specified in slot 2 of Table II, namely a delivery rate of 25 milligrams per hour for a two hour period, in this case from 3:00 a.m. to 5:00 a.m. Similarly, bars 114, 116 and 118 are graphical representations of the total drug delivery rates specified in time slots 3, 4 and 5, respectively, in Table II. While the total height of bars 110-118 represents the total drug delivery rate in each time period, cross-hatched area 120 represents the basal delivery rate of 20 milligrams per hour. The portion of bar 110 which extends above basal rate area 120 represents the interval rate for time slot 1 in Table II. Similarly, the portion of bars 112, 116 and 118 which extend above basal rate area 120 represents the interval rate for time slots 2, 4 and 5 in Table II. Since the interval rate for time slot 3 in Table II is zero, no portion of bar 114 extends above basal rate area 120.

Illustrated in a graphical manner, it is easy to visualize the basal rate and each individual interval for each individual time slot and to judge to effect on the overall dosage contributed by an individual time slot. Drug infusion system 12 communicates the graphical representation illustrated in FIG. 3 to the medical professional for use in determining what adjustments, if any, to make to the programmed drug regimen and for use if initially constructing a drug regimen, if so desired.

In a preferred embodiment, the medical professional may utilize the graphical representation as illustrated in FIG. 3 to construct and adjust the programmed drug regimen. It is preferred that the medical professional be allowed to graphically create and modify individual time segments, adjust starting and ending times and adjust the height of the bars to determine the particular drug regimen programmed or to be programmed. If is preferred that the basal rate, as illustrated by basal rate area 120, be allowed to be modified.

Should controller 32 calculate a daily dose, for example, which exceeds, or differs from, a maximum daily dose, or a preferred daily dose, the graphical representation as in FIG. 3 may be altered to show the medical professional what the altered drug regimen would look like and allow the medical professional to accept, reject or adjust the drug regimen directly on the graphical representation.

While the embodiments of the present invention have been described in terms of an implantable drug infusion device, it is to be recognized and understood that the features of the present invention could also be implemented in a non-implanted (or non-implantable) device. The only difference could be the method of communication between memory unit 26 and programmer 20. In fact, with a non-implanted device, programmer 20 and memory unit 26 could be combined into a single unit since communication by telemetry, or other wireless communication method, would no longer be necessary.

Thus, embodiments of a drug infusion system programmable in flex mode are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A drug infusion system capable of delivering a fluid medication to a patient under direction of a medical professional, comprising:
a drug delivery module capable of delivering said fluid medication to said patient continually at a basal rate and capable of delivering said fluid medication at an interval rate in each of a plurality of time slots over a specified period of time, said interval rate being different from said basal rate;
a controller, programmable by said medical professional, operatively coupled to said drug delivery module to control said basal rate and said interval rate at which said fluid medication is delivered to said patient;
wherein said controller, upon being pre-programmed by said medical professional to deliver an interval rate for at least one of said plurality of time slots, calculates a total dose of said fluid medication to be delivered to said patient over said period of time based on said basal rate and said interval rate for each of said plurality of time slots, compares said total dose against a maximum dose and calculates an adjusted basal rate, if necessary, so that said total dose does not exceed said maximum dose; and
a display, operatively coupled to said controller, configured to communicate said adjusted basal rate to said medical professional.

2. A drug infusion system as in claim 1 wherein said total dose equals said maximum dose.

3. A drug infusion system as in claim 1 wherein said interval rate may be programmed individually for each of said plurality of time slots.

4. A drug infusion system as in claim 1 wherein said period of time is a day, wherein said total dose is a daily dose and wherein said maximum dose is a desired daily dose.

5. A drug delivery device as in claim 4 wherein at least two of said plurality of time slots are of equal duration.

6. A drug infusion system as in claim 1 wherein said controller provides a graphical display of said interval rate in each of said plurality of time slots.

7. A drug infusion system as in claim 6 wherein said controller provides said graphical display to said medical professional.

8. A drug infusion system as in claim 1 wherein said drug delivery module is implantable.

9. A drug infusion system capable of delivering a fluid medication to a patient under direction of a medical professional, comprising:
a drug delivery module capable of delivering said fluid medication to said patient continually at a basal rate and capable of delivering said fluid medication at an interval rate in each of a plurality of time slots over a specified period of time, said interval rate being different from said basal rate;
a controller, programmable by said medical professional, operatively coupled to said drug delivery module to control said basal rate and said interval rate at which said fluid medication is delivered to said patient; and
wherein said controller, upon being pre-programmed by said medical professional to deliver an interval rate for at least one of said plurality of time slots and a total dose of said fluid medication to be delivered to said patient over said period of time, calculates an adjusted basal rate of said fluid medication based on said total dose and said interval rate for each of said plurality of time slots.

10. A drug infusion system as in claim 9 wherein said total dose equals a maximum dose.

11. A drug infusion system as in claim 9 wherein said interval rate may be programmed individually for each of said plurality of time slots.

12. A drug infusion system as in claim 9 wherein said controller provides a graphical display of said interval rate in each of said plurality of time slots.

13. A drug infusion system as in claim 9 further comprising a display configured to communicate said adjusted basal rate to said medical professional.

14. A drug infusion system as in claim 9 wherein said drug delivery module is implantable.

15. A drug infusion system as in claim 9 further comprising a display configured to communicate said adjusted basal rate to said medical professional.

16. A method of delivering a fluid medication from an implanted device to a patient under direction of a medical professional, said implanted device being part of a system, comprising the steps of:
manually programming said implanted device with a preferred dose, a basal rate and a plurality of interval rates over a specified period of time, each individual one of said interval rates corresponding to an individual one of a plurality of time slots during said specified period of time;
said system calculating a total dose over said specified period of time based on said basal rate and said interval rates, each individual one of said interval rates corresponding to an individual one of said plurality of time slots;

said system calculating an adjusted basal rate so that said total dose does not exceed said preferred dose; and communicating said adjusted basal rate to said medical professional.

17. A method of delivering a fluid medication as in claim 16 wherein said total dose equals said preferred dose.

18. A method of delivering a fluid medication as in claim 16 wherein said plurality of interval rates may be programmed individually for each of said plurality of time slots.

19. A method of delivering a fluid medication as in claim 16 wherein said controller provides a graphical display of said interval rates in each of said plurality of time slots.

20. A method of delivering a fluid medication from an implanted device to a patient under direction of a medical professional, said implantable medical device being part of a system, comprising the steps of:

manually programming said implanted device with a basal rate and a plurality of interval rates over a specified period of time, each individual one of said interval rates corresponding to an individual one of a plurality of time slots during said specified period of time;

said system calculating a total dose over said specified period of time based on said basal rate and said interval rates;

manually adjusting at least one of said plurality of interval rates;

said system calculating an adjusted basal rate in accordance with said plurality of interval rates as adjusted in said manually adjusting step; and communicating said adjusted basal rate to said medical professional.

* * * * *